United States Patent
Cowe et al.

(10) Patent No.: US 10,485,932 B2
(45) Date of Patent: Nov. 26, 2019

(54) NEEDLE ASSEMBLY

(71) Applicant: Owen Mumford Limited, Oxford (GB)

(72) Inventors: Toby Cowe, Oxford (GB); Oliver Anderson, Oxford (GB)

(73) Assignee: Owen Mumford Limited, Oxford (GB)

( * ) Notice: Subject to any disclaimer, the term of this patent is extended or adjusted under 35 U.S.C. 154(b) by 216 days.

(21) Appl. No.: 15/503,321

(22) PCT Filed: Jul. 31, 2015

(86) PCT No.: PCT/GB2015/052224
§ 371 (c)(1),
(2) Date: Feb. 10, 2017

(87) PCT Pub. No.: WO2016/024085
PCT Pub. Date: Feb. 18, 2016

(65) Prior Publication Data
US 2017/0232205 A1    Aug. 17, 2017

(30) Foreign Application Priority Data

Aug. 12, 2014    (GB) .................................. 1414297.0

(51) Int. Cl.
| A61M 5/32 | (2006.01) |
| A61M 5/42 | (2006.01) |
| A61M 5/00 | (2006.01) |

(52) U.S. Cl.
CPC .......... *A61M 5/3202* (2013.01); *A61M 5/002* (2013.01); *A61M 5/326* (2013.01);
(Continued)

(58) Field of Classification Search
CPC ........ A61M 5/3202; A61M 2005/3247; A61M 2005/3267; A61M 5/002; A61M 5/3243;
(Continued)

(56) References Cited

U.S. PATENT DOCUMENTS

| 2002/0014430 A1 | 2/2002 | Groth |
| 2005/0269227 A1 | 12/2005 | Erickson |

(Continued)

FOREIGN PATENT DOCUMENTS

| DE | 102004025651 | 12/2005 |
| EP | 2572746 | 3/2013 |

(Continued)

OTHER PUBLICATIONS

International Search report and Written Opinion issued in corresponding PCT Application No. PCT/GB2015/052224, dated Jan. 27, 2016, 19 pages.
(Continued)

*Primary Examiner* — Rebecca E Eisenberg
(74) *Attorney, Agent, or Firm* — Quarles & Brady LLP

(57) ABSTRACT

A needle assembly is disclosed, for use with an injection device. The needle assembly comprises a needle hub (20) having a needle (22) and a needle shield (40) arranged for relative axial movement with respect to the needle hub, between a retracted position in which the tip of the needle projects beyond a forward end of the shield and an extended position in which the tip of the needle does not project beyond the forward end of the shield. The needle shield (40) is axially biased towards the extended position. The needle shield (40) is further arranged to be torsionally biased for relative rotational movement with respect to the needle hub (20).

20 Claims, 15 Drawing Sheets

(52) U.S. Cl.
CPC ........ *A61M 5/3245* (2013.01); *A61M 5/3272* (2013.01); *A61M 5/422* (2013.01); *A61M 2005/3247* (2013.01); *A61M 2005/3267* (2013.01)

(58) Field of Classification Search
CPC ... A61M 5/3245; A61M 5/326; A61M 5/3272
See application file for complete search history.

(56) References Cited

U.S. PATENT DOCUMENTS

| | | |
|---|---|---|
| 2009/0024093 A1 | 1/2009 | Carrel |
| 2011/0160675 A1 | 6/2011 | Ruan et al. |
| 2013/0105345 A1 | 5/2013 | Van der Beek |
| 2014/0076758 A1 | 3/2014 | Dasbach |
| 2014/0097111 A1 | 4/2014 | Dasbach |
| 2014/0228772 A1* | 8/2014 | Ward .................... A61M 5/326 604/198 |
| 2014/0236100 A1* | 8/2014 | Ward .................... A61M 5/326 604/263 |

FOREIGN PATENT DOCUMENTS

| | | |
|---|---|---|
| WO | 99/22790 | 5/1999 |
| WO | 2010/019936 | 2/2010 |
| WO | 2010/110743 | 9/2010 |
| WO | 2010/126432 | 11/2010 |

OTHER PUBLICATIONS

United Kingdom Search Report issued in corresponding United Kingdom Patent Application No. 1414297.0, dated Feb. 10, 2015, 1 page.

* cited by examiner

NEEDLE ASSEMBLY

CROSS-REFERENCE TO RELATED APPLICATIONS

This application represents the U.S. National Stage of International Application No. PCT/GB2015/052224 filed Jul. 31, 2015, which is incorporated by reference in its entirety and is based on, claims priority to, and incorporates herein by reference in their entireties, British Patent Application Serial Nos. GB 1414297.0, filed Aug. 12, 2014.

This invention relates to a needle assembly, and in particular, but not exclusively, to a single-use disposable needle assembly.

Injection devices, such as the Owen Mumford Autopen®, are commonly used by patients to self-administer injections of medicament. Such devices are typically provided in a pen-like body which contains, defines or receives a cartridge or syringe of medicament. The injection device generally comprises a delivery mechanism which is arranged to dispense the medicament via a needle in response to a user pressing a button or trigger.

As many such injection devices are arranged to be either reusable (i.e. the cartridge of medicament can be replaced) or to deliver a plurality of separate injections until the medicament within the device has been fully consumed it is common to arrange the device to receive a disposable, single-use, needle (which may be referred to as a "pen needle"). It is known to provide such needles as a needle assembly which includes both a hub, which carries the needle and is arranged to be removably attached to the device (or syringe of the device) in use, and a shield member which is arranged to cover the needle prior to and/or after use to reduce the risk of accidental needle-stick injuries during use. One such arrangement is, for example, disclosed in Published US Patent Application US2009/0259178 A1.

Whilst it may be desirable to provide a pen needle assembly which includes a shielding arrangement this must be balanced with the requirement that a pen needle is generally a disposable single use article. Thus, it would be advantageous if a pen needle assembly including a needle shield did not significantly increase the part-count and/or complexity of the needle assembly and/or any associated packaging (which must generally maintain the sterility of the needle assembly prior to use). At least some embodiments of the invention seek to provide an improved needle assembly which may help to address some of these problems.

According to one aspect of the invention, there is provided a needle assembly, for use with an injection device, the needle assembly comprising:

a needle hub having a needle;

a needle shield arranged for relative axial movement with respect to the needle hub, between a retracted position in which the tip of the needle projects beyond a forward end of the shield and an extended position in which the tip of the needle does not project beyond the forward end of the shield, the needle shield being axially biased towards the extended position; wherein the needle shield is further arranged to be torsionally biased for relative rotational movement with respect to the needle hub.

It will be appreciated that references to the forward end (or direction) of the needle assembly (or components thereof) refer to the end of the needle assembly which is intended to face the injection site in use.

The needle hub may be configured to be attachable to an injection device. For example, the needle hub may be provided with an internal screw thread. The needle assembly may typically be a single use, disposable, item (which may for example be used with a reusable injection device).

It will be appreciated that the needle shield is arranged to prevent accidental needle stick injuries before and/or after use. The needle assembly may lock the needle shield after use to prevent injuries and/or re-use of the needle assembly.

The needle assembly may have a spring member which is arranged to both torsionally and axially bias the needle shield relative to the needle hub. For example, the spring member may be a coil spring. Using a single spring member to actuate both rotational and axial movements of the needle shield relative to the needle hub may reduce the part-count and or overall complexity of the needle assembly. For example, the needle assembly according to some embodiments may advantageously consist of only three parts.

The needle shield and needle hub may be provided with cooperating features for controlling the relative movement thereof. The cooperating features may be configured such that relative rotational movement of the needle shield relative to the needle hub is prevented until the needle shield moves towards the retracted position. For example, the cooperating features may be arranged such that the axial bias must be compressed before the rotational bias may rotate the shield. The needle shield may be initially held against the torsional bias by the cooperating features. The cooperating features may be arranged such that axial movement of the needle shield relative to the needle hub releases the needle shield for automatic rotational movement under the torsional bias.

The cooperating features may be configured such that in an initial position relative rotation of the needle shield and needle hub is limited to a first rotational alignment. In the initial position the shield may be in its extended position.

The cooperating features may further be configured such that axial movement of the needle shield rotationally releases the needle shield and needle hub to allow relative rotation. The axial movement may be towards the retracted position. The relative rotation (after release) may be in the biased direction toward a second rotational alignment.

The cooperating features may be further configured such that upon return of the needle shield to the extended position the rotational bias prevents return of the needle shield and needle hub to said first rotational alignment. Thus, the cooperating features may retain the needle shield and needle hub in said second rotational alignment. Upon return of the needle shield to the extended position further relative axial movement may be prevented by an axial stop. For example, the torsional bias may provide relative rotational movement between the hub and shield which aligns the cooperating features with the axial stop.

The cooperating features may comprise cooperating formations. The cooperating features may, for example, comprise a track associated with one of the needle hub or the needle shield and a cooperating projection associated with the other of the needle hub or the needle shield. The projection may be a radial extending projection.

For example an outwardly radially extending projection may be provided on the needle hub. The track may be formed on an inner surface of the needle shield. This may, for example, enable the needle hub to be contained within the needle shield.

The projection may comprise a resiliently deformable leg. In use, the leg may be displaced to allow relative rotational movement of the needle shield relative to the needle hub. A portion of the track may comprise a ramp or cam surface arranged to displace the leg. For example, the ramp or cam surface may be arranged to allow the projection to move between a first and second track section (for example, by rotation under the force of the torsional bias).

A plurality of said cooperating features (for example a plurality of projections and cooperating tracks) may be provided at circumferentially spaced locations. A plurality of cooperating features may, for example, provide improved stability between the needle hub and needle shield.

The needle assembly may be provided with a textured surface arranged to engage the skin during use. Such textured surfaces may act to mask the injection pain. Thus, a forward facing surface of the needle shield may comprise a textured surface. The textured surface may surround an aperture in the forward face of the needle through which the needle projects in use. The textured surface may comprise a plurality of forwardly projecting spikes. For example the spikes may be arranged in at least one concentric ring around the aperture.

Advantageously, providing the textured surface on the needle shield allows the rotation provided by the torsional bias during injection use to cause the textured surface to rotate against the skin. In embodiments of the invention the shield rotates under the torsional bias as the shield is retracted. The forward surface of the needle shield may be arranged to rotate whilst in contact with the skin prior to the needle projecting beyond the shield (to pierce the skin) and, thus, provides a masking stimulus. This is particularly so where the forward surface is textured.

The needle hub and needle may be fully contained within the needle shield when the shield is in the extended position. This may enable the outer surface of the needle shield to be the main sterile barrier for the needle assembly.

According to another aspect of the invention, there is provided a needle assembly, for use with an injection device, the needle assembly comprising:

a needle hub having a needle;

a needle shield arranged for relative axial movement with respect to the needle hub, between a retracted position in which the tip of the needle projects beyond a forward end of the shield and an extended position in which the tip of the needle does not project beyond the forward end of the shield; and wherein the needle hub and needle shield are configured such that, when the needle shield is in the extended position, the rearward end of the needle hub is forward of the rearward end of the needle shield.

The needle shield may typically be axially biased towards the extended position (and may, for example, additionally include one or more features from the above embodiments).

The needle shield may be longer in the axial direction than the combined axial length of the needle hub and needle. It will be appreciated that the axial direction of the needle assembly, and components thereof, will generally be the direction in which the needle is orientated.

The needle shield may extend from a substantially closed forward face. The closed forward face may include an aperture, through which the needle extends in use. The needle shield may extend to a substantially open rearward face.

The needle hub may be captive between the forward and rearward faces of the needle shield. In other words, the needle hub and needle shield may be arranged to slide axially relative to one another but the needle hub may be arranged such that it cannot move beyond, or be removed from, the interior of needle shield. It will be appreciated that the interior of the needle shield may be defined by the forward and rearward faces and side walls of the needle shield and the outer. The needle hub and needle shield may be arranged such that the needle hub and needle are entirely between the faces of the needle shield when the shield is in the extended position.

At least one of the faces of the needle shield may be provided with a removable closure. The closure may be arranged to be removed prior to use by the end user. The closure may provide a sterile seal. The closure may be a "tear-off" flexible membrane. Alternatively, the closure may be a resilient member or cap.

The needle shield may be provided with a stop proximal to its rearward end to delimit the range of relative axial movement between the needle shield and needle hub. The needle shield may further be provided with a stop at its forward end (for example the forward stop could simply comprise the inner surface of the closed front face). The, or each, stop may cooperate with a corresponding feature of the needle hub. The cooperating feature could, for example, comprise a rearward or forward shoulder of the needle hub.

The needle shield defines a continuous outer sidewall (extending between the forward and rearward faces) which encloses the needle hub. The sidewall may be defined by a continuous circumferential surface. The sidewall may provide a sterile outer barrier around the needle and needle hub prior to use (such that only the forward and rearward faces need be provided with a sterile seal). The sidewall may additionally mask or hide the needle from the user (which is particularly advantageous, for example, for users with needle phobia).

The needle assembly may be packaged in a flexible airtight wrapping. For example the wrapping may be a "flow-wrap" type packaging (which may also be referred to as a crimp seal wrapping). The flexible wrapping may be sterile. The flexible wrapping may be tearable by the end-user. The use of such a simple packaging arrangement is not generally possible with existing needle assemblies due to the risk of the needle piercing the packaging resulting in needle stick injuries and/or loss of sterility. However, in embodiments of the invention the needle is, prior to use, captive within the needle shield and cannot be moved beyond the initial position as no portion of the needle or hub extends beyond the rear of the needle shield (to provide a surface which could push the needle forward relative to the needle shield).

The needle assembly may further comprise a removable cap member arranged to seal the needle assembly prior to use. The cap member may comprise first and second axially spaced apart covers configured in use to close the end faces of the needle assembly. Thus, if the needle shield forms the main sterile barrier the cap may act to close the needle shield.

This may be advantageous in its own right, thus according to a further aspect of the invention there is provided a needle assembly for use with an injection device, the needle assembly comprising: a needle hub having a needle; a needle shield arranged for relative axial movement with respect to the needle hub and a removable cap comprising first and second axially spaced apart covers configured in use to close the end faces of the needle assembly. The needle hub and needle may be fully contained within the needle shield when the shield is in the retracted position.

The cap may be substantially U-shaped. The covers may be substantially radially extending. The covers may sealingly engage the radial end faces of the needle assembly (for example the radial end faces of the needle shield of the needle assembly). The cap may be arranged to engage/disengage the needle assembly in a radial direction. Advantageously, this may avoid any axial force being applied which might act to pull the needle shield/needle hub apart during removal.

The cap may be arranged to resiliently engage the needle assembly. For example the cap may snap fit onto the needle assembly. This may, for example, enable the cap to be re-engaged with the needle assembly after use (for example to re-seal and/or protect against needle injuries).

Needle assemblies according to embodiments of the invention may be provided as a plurality of disposable needles such that a user has a convenient supply and/or can track usage. According to a further aspect of the invention there is provided a kit comprising: a plurality of needle assemblies in accordance with an embodiment; and a storage tray comprising a plurality of recesses each configured to removably receive a needle assembly. Each needle assembly may be sealingly received into a recess prior to use. Thus, a sterile seal may be provided between the tray and needle assembly without the need to provide a separate sterile seal on that portion of the needle assembly. Thus, for example, only a single individual sterile seal may be required on each needle assembly.

Thus, according to a further aspect of the invention there is provided a method of packaging a plurality of needle assemblies, the method comprising: sealingly engaging a first end of each needle assembly into a tray; and individually sealing the second end of each needle assembly. The method may further comprise the step of sterilising the plurality of needle assemblies and tray. For example, the assembled tray and needles may be subjected to gamma irradiation.

Whilst the invention has been described above with reference to a number of embodiments and aspects it is to be understood that it includes any inventive combination of the features set out above or in the following description or drawings.

Specific embodiments of the invention will now be described in detail, by way of example only, and with reference to the accompanying schematic drawings in which.

Front as used herein will be understood to refer to the end of the pen needle assembly (or components thereof) which is, in use, pointed at the skin. Rear as used herein will be understood to refer to the end of the pen needle assembly (or components thereof) which is, in use, distal from the skin. Forward and rearward will, likewise, be understood to refer to the directions orientated towards the front and rear of the pen needle assembly.

Figure 1A:
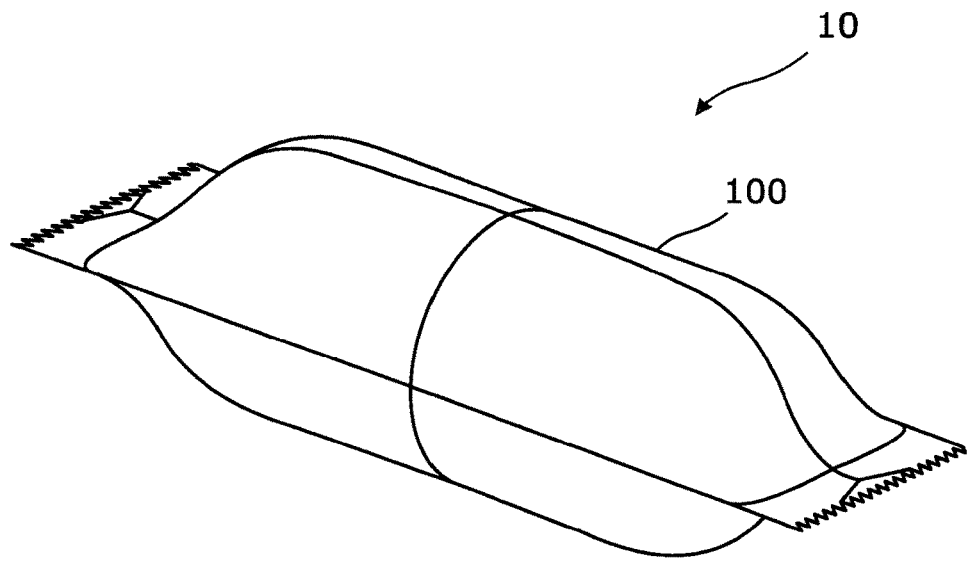
FIG. 1 shows a three dimensional representation and cross section of a needle assembly and packaging in accordance with an embodiment of the invention.
Figure 1B:
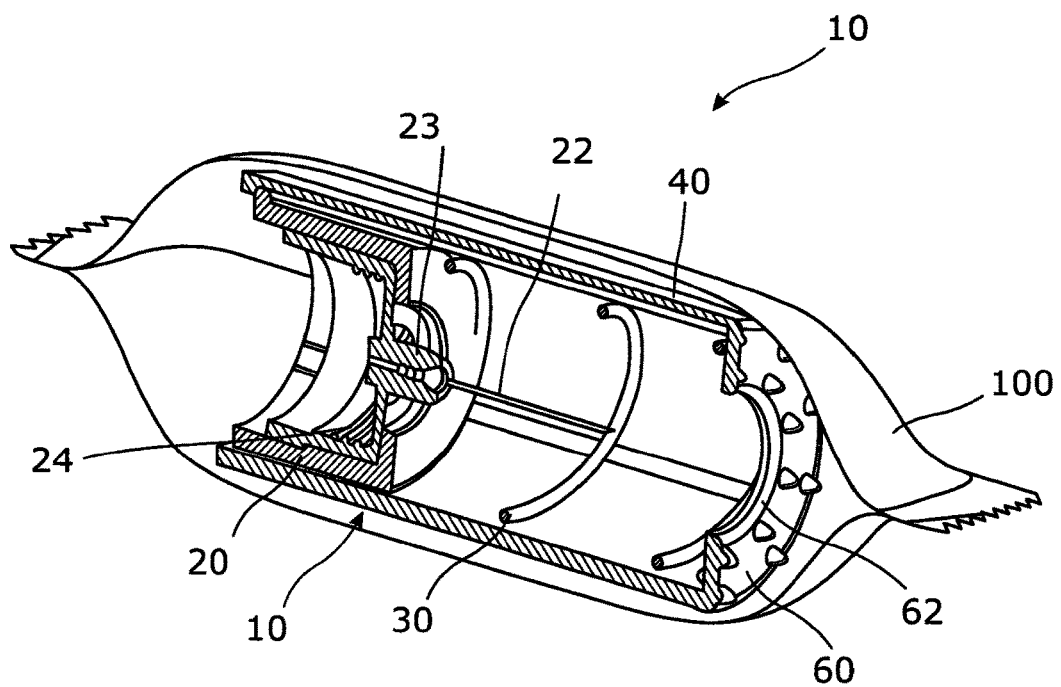

A needle assembly 10 is shown in FIG. 1 contained within a flow wrap sterile packaging 100 in a typical configuration in which the needle assembly 10 may be initially supplied to a user. The needle assembly 10 includes a needle hub 20 which carries a needle 22 (which may be a double ended needle with a forward projecting portion for piercing the skin and a rearward projecting end for piercing the septum of an injection device). An interconnecting arrangement such as an internal thread 24 is provided on the hub 20 to allow attachment of the needle assembly to an injection device. It may be noted that in the embodiment of FIG. 1 the hub 20 has a two part construction but it will be appreciated that this is an optional arrangement (for example in the embodiment of FIG. 2 the hub 20 is formed as a single moulding). The needle assembly 10 further comprises a needle shield 40 which is relatively moveable with respect to the needle hub between the extended position shown in FIG. 1 (in which the needle is covered and which may, therefore, alternatively be referred to as a shielded position) and a retracted position in which the needle 22 will project beyond the forward surface 60 of the needle shield 40 through the aperture 62 (and which may, therefore, alternatively be referred to as a delivery position). A coil spring 30 is provided between the hub 20 and shield 40 and, as will be explained in further detail below, is arranged to axially bias the shield 40 towards the extended position and to torsionally bias the shield 40 relative to the hub 20. In the supplied state it may be noted that the needle hub 20 and needle 22 are both fully contained within the needle shield 40 as the needle shield extends both forward beyond the tip of the needle and rearward beyond the rear surface of the hub 20. This ensures that the needle and hub are fully protected by the shield and enables the use of a simple flow wrap type packaging without the need to additionally protect/enclose the needle.

Figure 2A:
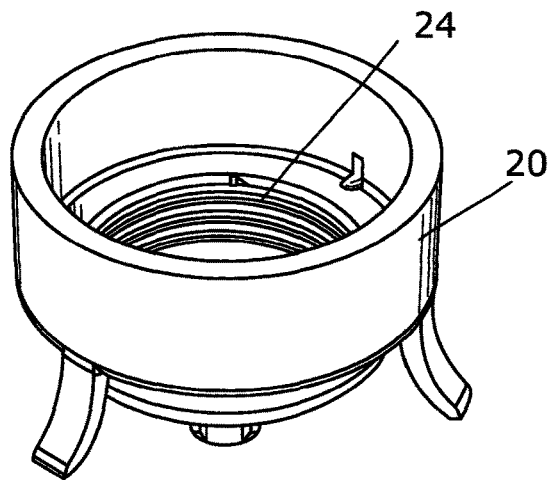
FIG. 2 shows three-dimensional views and a front view of a needle hub component for use in an embodiment.
Figure 2B:
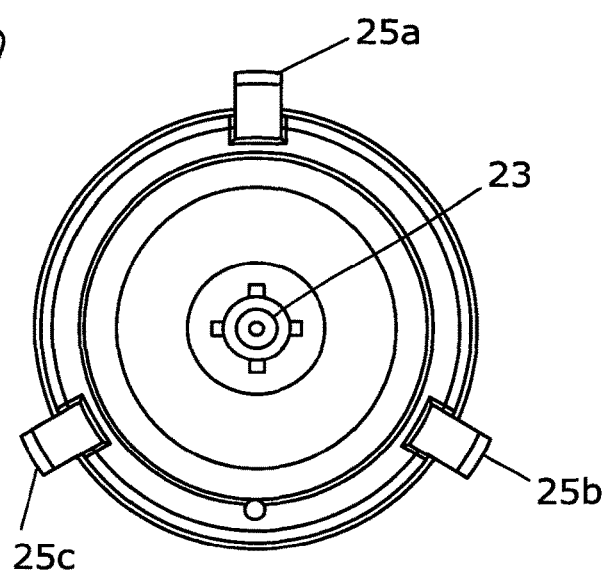
Figure 2C:
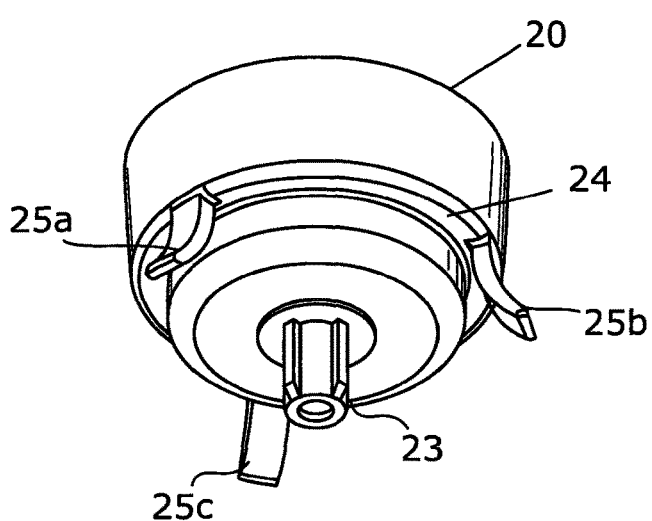
Figure 3A:
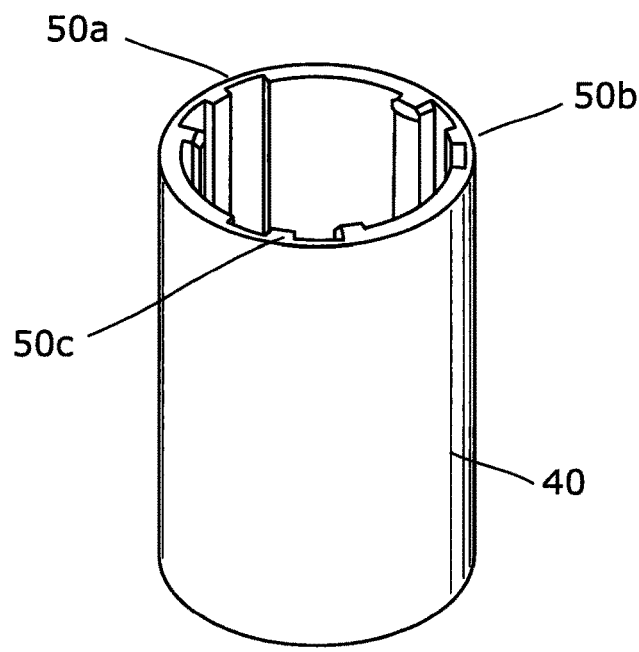
FIG. 3 shows three-dimensional views, a front view, a top view and a cross section of a needle shield component for use in an embodiment.
Figure 3B:
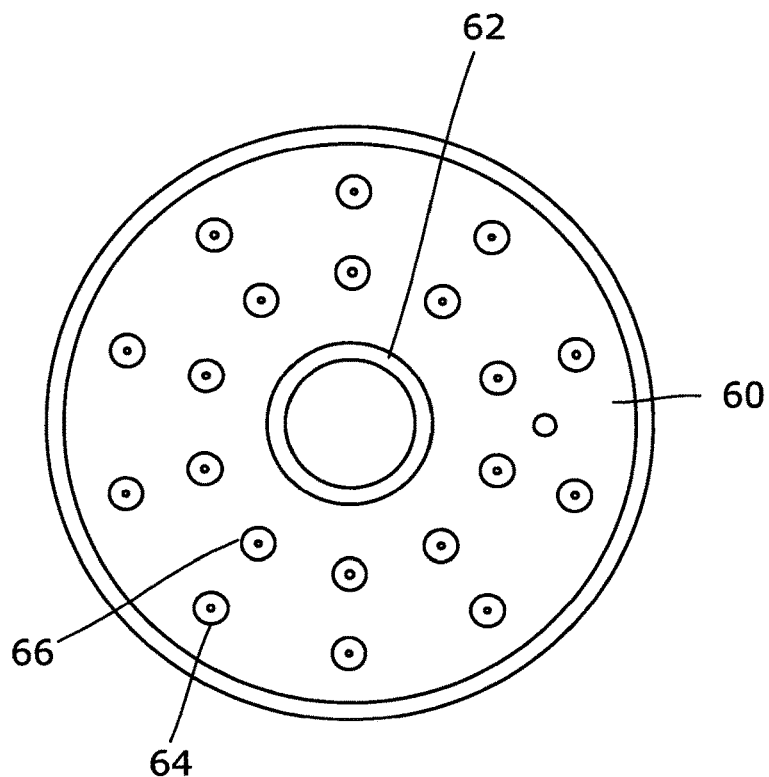
Figure 3C:
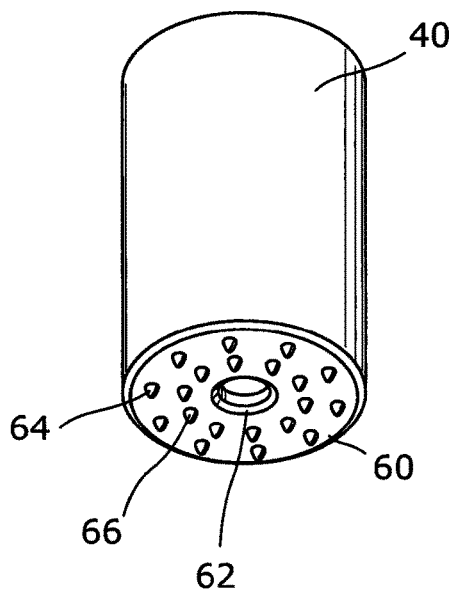
Figure 3D:
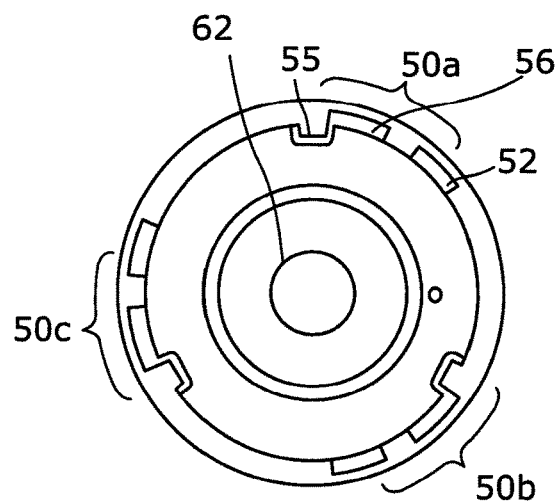
Figure 3E:
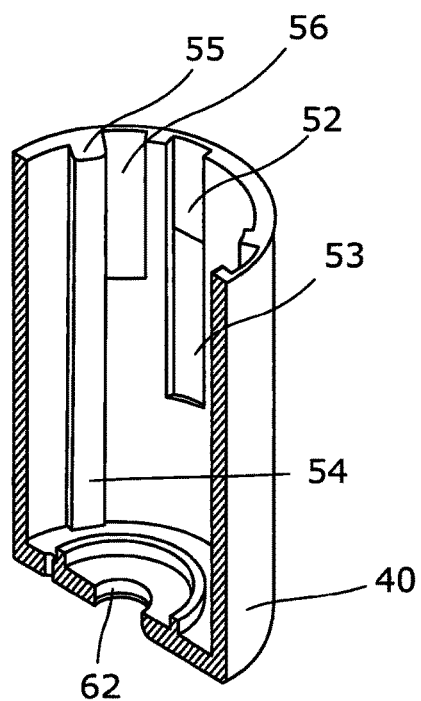

The hub 20 is shown in isolation in FIG. 2. As noted above, in this embodiment the hub 20 is formed as a single moulding and includes a needle support 23 into which the needle 22 is permanently attached (for example by bonding or plastic welding). The needle 22 is standard and has been omitted from FIGS. 2 to 8 for clarity (since the key features of the embodiments are formed in the needle hub 20 and shield 40).

The needle hub 20 is provided with features, in the form of radially outwardly splaying legs 25 which project from a radial shoulder 24. The legs 25 cooperate with corresponding features on the needle shield to control the relative movement of the needle shield 40 and needle hub 20. As will be explained below, the legs are inwardly resiliently deformable. It will be appreciated that whilst the illustrated embodiment has three circumferentially distributed legs 25a, 25b and 25c more or less legs may be provided as convenient (balancing the requirements of stability of the needle hub 20 relative to the needle shield 40 and the overall manufacturing complexity of the needle assembly 10).

The needle shield 40 is shown in FIG. 3 and comprises a generally cylindrical outer body having a forward surface 60 (which abuts the users skin in use) and an open rearward end into which the needle hub 20 is received. An aperture 62 is provided at the centre of the forward surface 60 through which the needle 22 will project during use. The inner surface of the shield 40 is provided with cooperating features for engaging with the legs 25 of the hub 20. As best seen in FIG. 3(e) each of the cooperating features is formed of a track 50(a), 50(b) and 50(c) arranged and configured to receive the respective leg 25. Each track comprises a first slot 52 which includes a ramp section 53, an axially extending rib 54 and a second slot 56. The operation of the track 50 and legs 25 will be described in further detail below.

The forward facing surface 60 of the shield 40 has a textured surface. The textured surface provides nerve stimulation to the skin immediately surrounding the injection site during use so as to mask the pain of the needle penetration. In particular, the textured surface may be formed by a series of spikes which are sized so as to provide sufficient stimulation of the skin without piercing the skin surface and may for example have dimensions of approximately 1 mm×1 mm with a 23° chamfer angle. In the illustrated example the spikes are arranged in a first 64 and second 66 concentric ring surrounding the needle aperture 62.

FIG. 4 shows the sequential operation of the needle apparatus in cross section (in particular to illustrate the interaction of the cooperating features). FIG. 4(a) shows the initial position, with the hub 20 in a first rotational alignment relative to the needle shield 40. The legs 25 are positioned within the first slot 52 of the track 50 and the spring 30 is biasing the hub 20 and shield 40 to their extended positions. It would be noted that the readily inward projection 55 provided at the end of the rib 54 engages the rearmost surface of the hub 20 so as to act as a stop which delimits the relative axial movement of the shield 40 and the hub 20. Thus, the hub 20 is retained captive within the shield 40. In this position, the coil spring 30 is also providing a torsional bias on the needle hub 20 but rotational movement of the hub 20 relative to the shield 40 is prevented as the width of the first slot 52 closely matches the width of the legs 25 and the slot is of sufficient depth to retain the legs therein. Thus, the legs 25 and first slot 52 of the track 50 hold the hub 20 and shield 40 in the first rotational alignment. As the injection device is pressed against the users skin and/or the syringe of the injection device is moved forward there is relative movement between the needle hub 20 and the needle shield 40 towards the retracted position of the needle shield as shown in FIG. 4(b). The legs 25 of the hub 20 initially travel along the first slot 52 and are resiliently deflected progressively inwardly by the ramp 53 formed in the slot 52 as they reach the forward axial end of the slot 52. This allows the legs to be released from the slot 52 freeing the hub 20 for rotation under the torsional force of the coil spring 30 towards the rib 54. The rib 54 provides a rotational stop to limit the extent of the relative rotation between the hub 20 and shield 40. The rib 54, therefore, defines (in cooperation with the leg 25) the second rotational alignment of the hub 20 and shield 40.

Figure 4A:
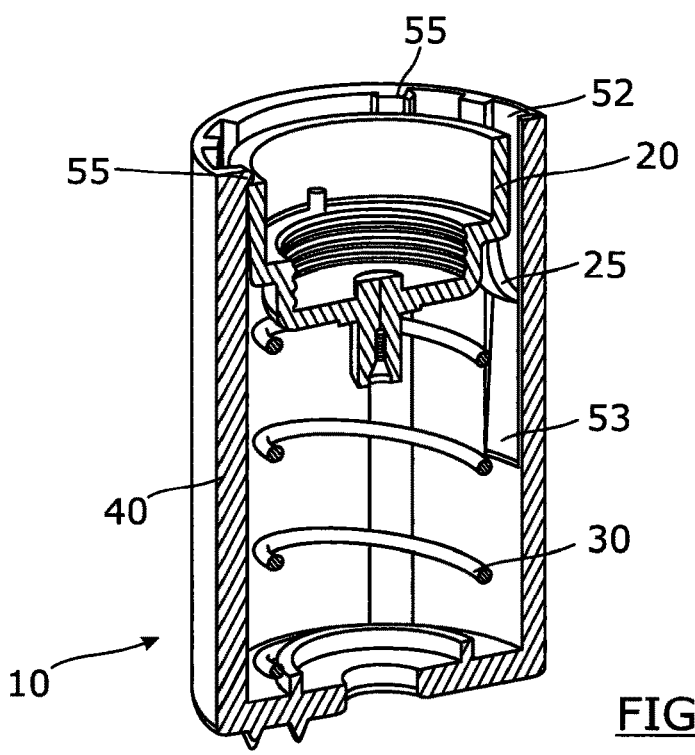
FIG. 4 is a cross sectional representation of the needle assembly according to an embodiment showing the sequential relative movement of the needle hub and needle shield during use.
Figure 4B:
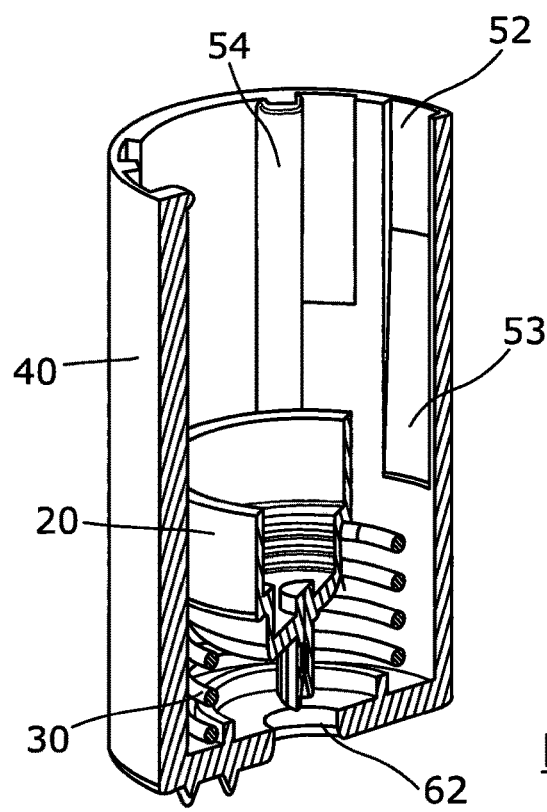
Figure 4C:
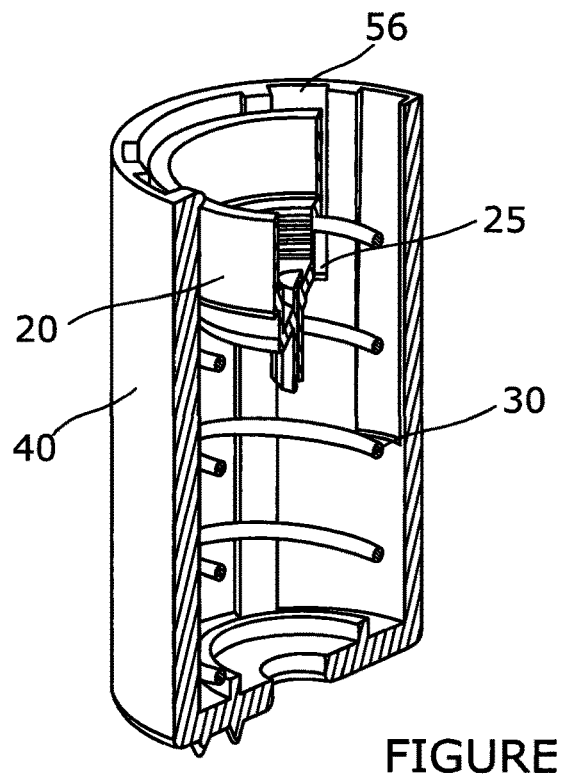
Figure 4D:
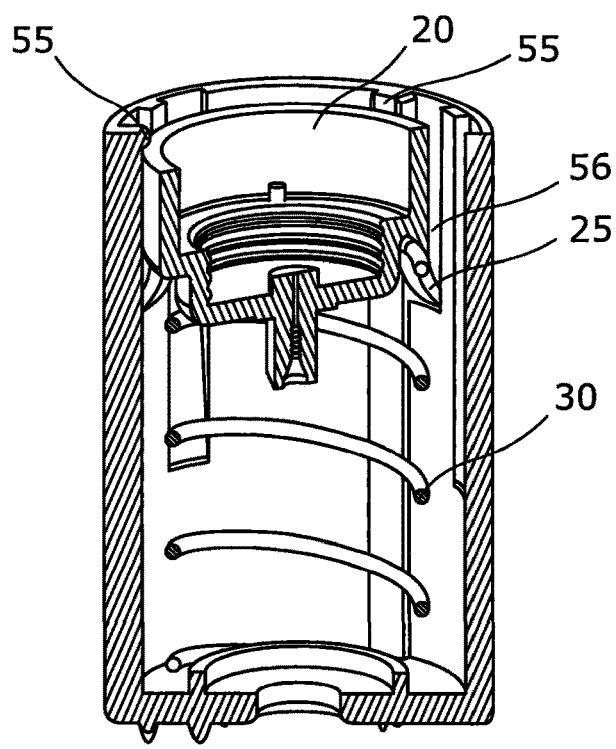
Figure 5A:
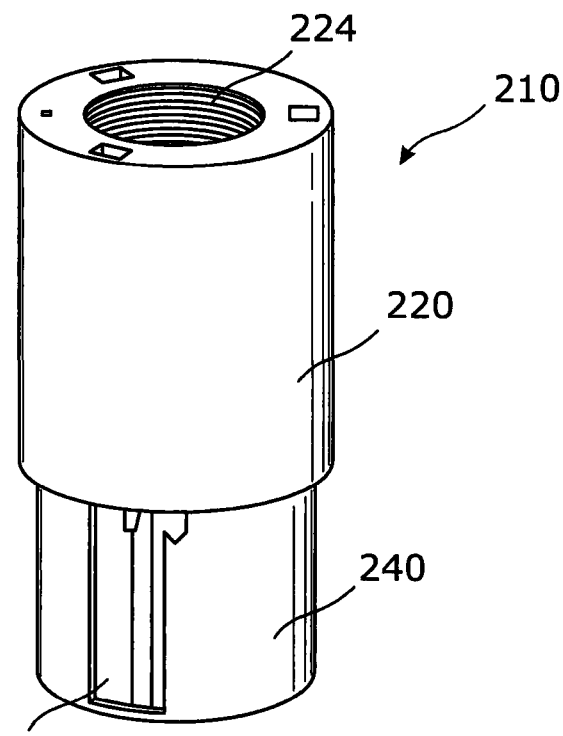
FIG. 5 shows a three dimensional view of needle assembly according to an alternative embodiment in a sequence of positions during use.
Figure 5B:
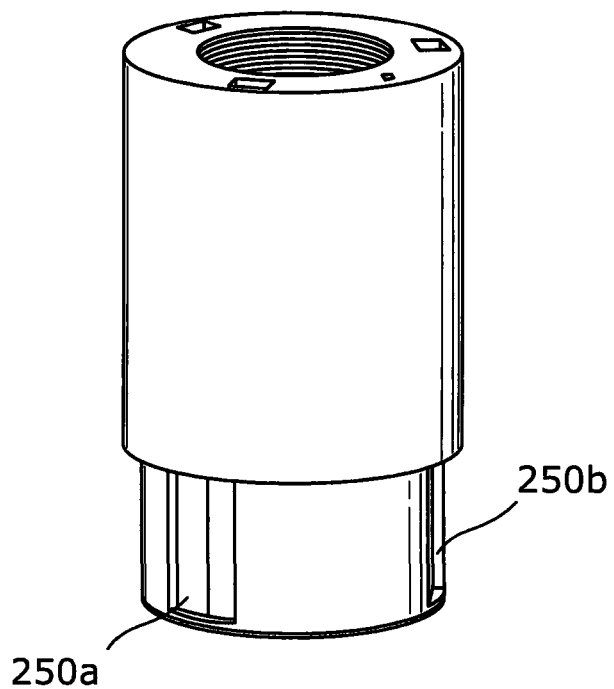
Figure 5C:
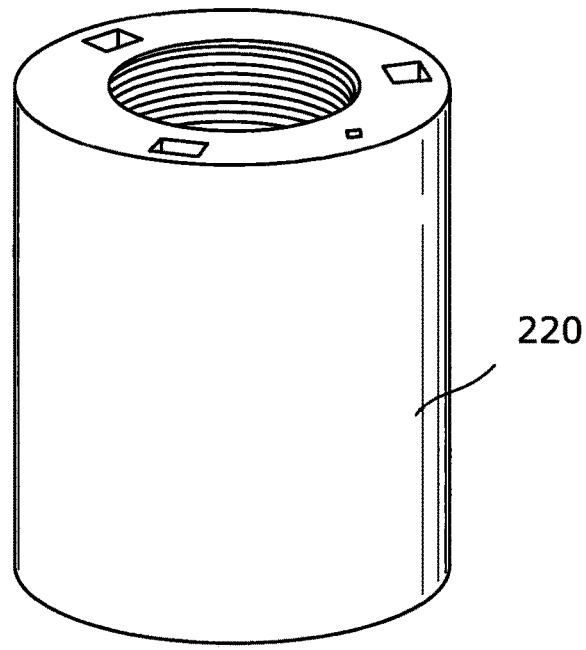
Figure 5D:
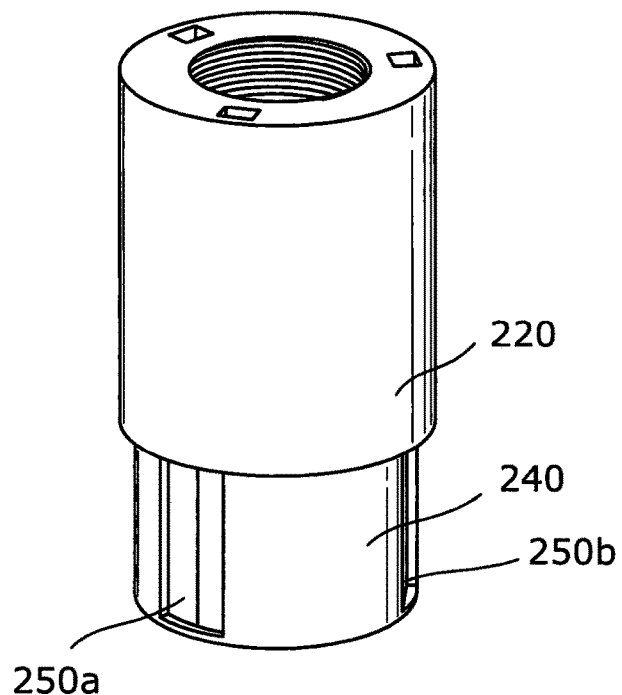

As the device is removed from the skin the compressed spring 30 axially biases the needle shield 40 and needle hub 20 apart so as to return the needle shield to its extended position, as shown in FIG. 4(c). Thus, the shield 40 returns to an axial position in which the needle is fully enclosed within the shield 40. Due to the torsional bias of the spring 30 the hub 20 and shield 40 remain in their second rotational alignment during the retraction movement with the legs 25 abutting the ribs 54. When the shield 40 has reached a sufficiently extended position the legs 25 move into alignment with the second slot 56 of the track 50. Due to the shape and resilience of the legs (which are inwardly deformed after leaving the first slot 52) the legs snap outwardly to be retained within the slot 56. The second slot 56 is formed with step sides and a flat base to help retain the legs 25 therein. The legs 25 cannot deform inwards so prevent the spring from being compressed and lock the needle hub 20 into its rearward position after use. It will also be noted that the projection 55 is once again in alignment with the rearward edge of the hub 20 so that rearward movement of the needle hub 20 relative to the needle shield 40 is also prevented.

Figure 6:
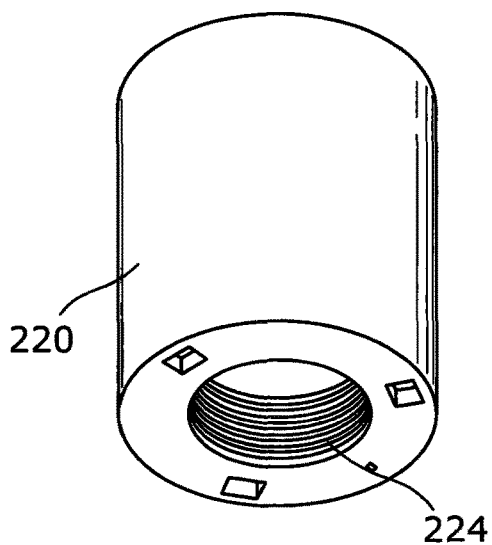
FIG. 6 shows three-dimensional views and a top view of a needle hub component for use in the embodiment of FIG. 5.
Figure 6B:
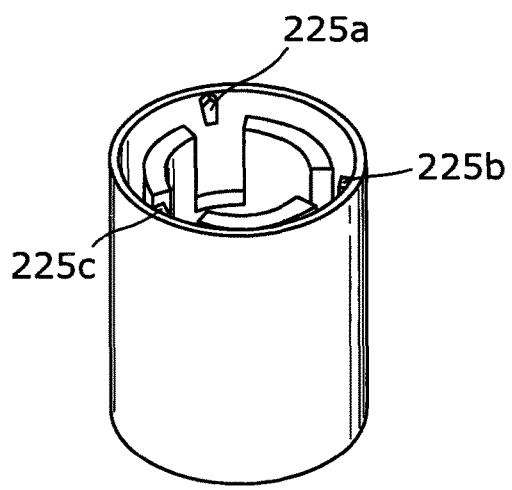
Figure 6C:
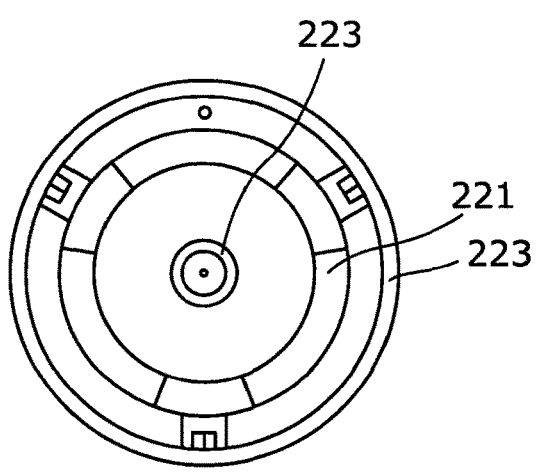
Figure 7A:
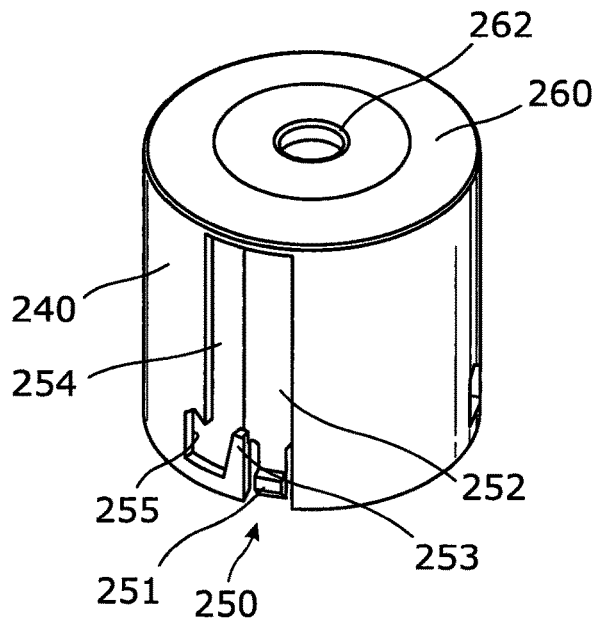
FIG. 7 shows three-dimensional views, a front view, a top view and a cross section of a needle shield component for use in the embodiment of FIG. 5.
Figure 7B:
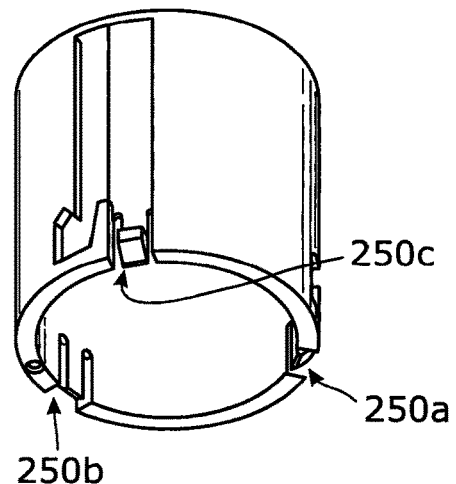
Figure 7:
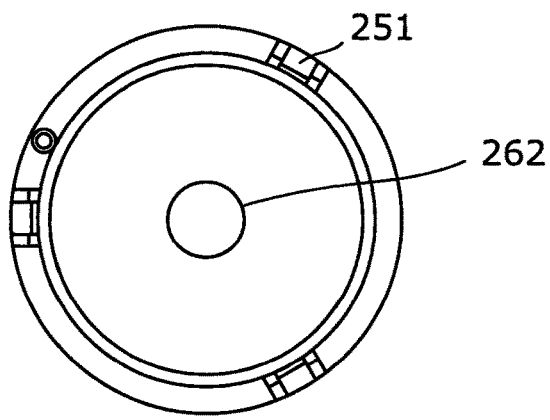
Figure 8A:
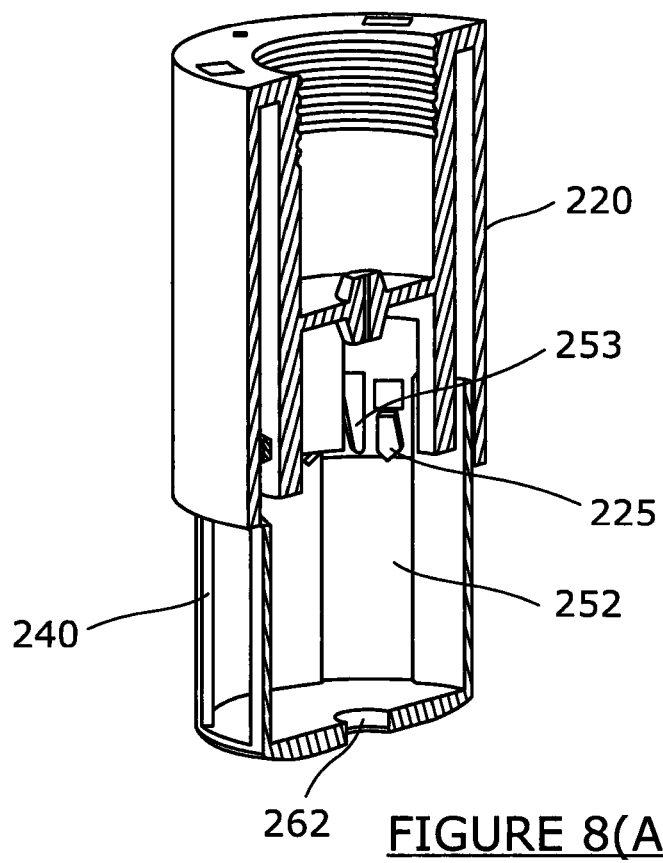
FIG. 8 is a cross sectional representation of the needle assembly of FIGS. 5 to 7 according to an embodiment showing the sequential relative movement of the needle hub and needle shield during use.
Figure 8B:
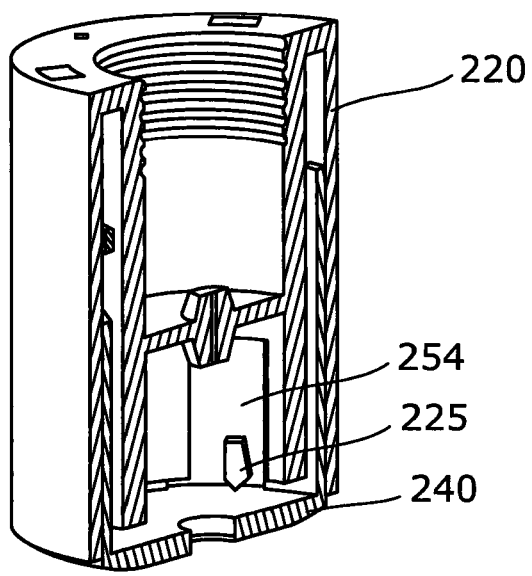
Figure 8C:
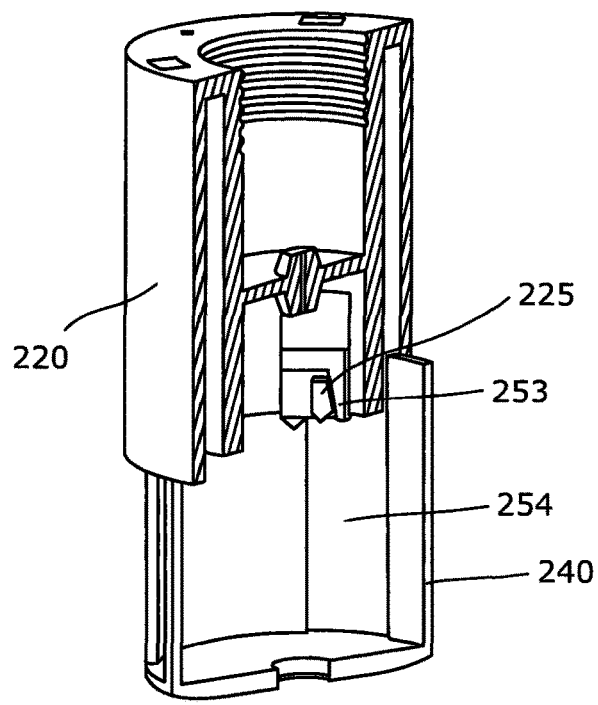
Figure 8D:
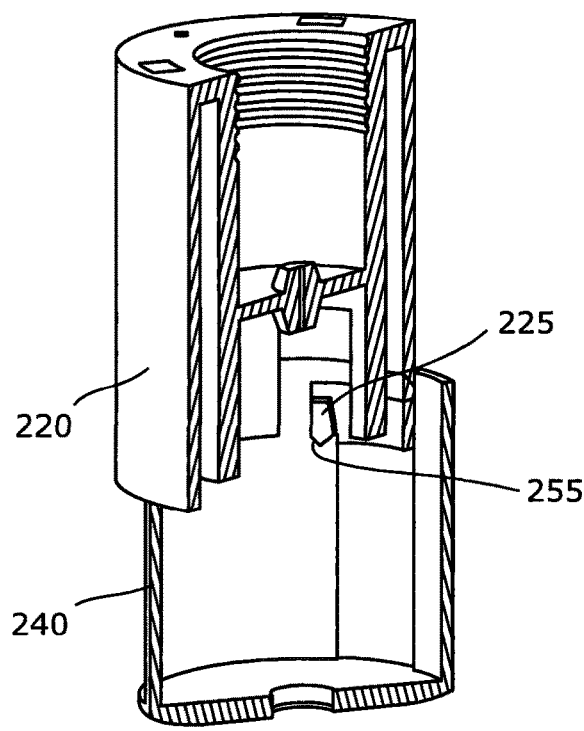

A needle assembly 210 according to a further embodiment is shown in FIG. 5 (with corresponding features generally indicated by reference numerals increased by 200). In this embodiment the needle hub 220 is provided with an inner 221 and outer 223 circumferential walls (as seen in FIG. 6) with the needle shield 240 received within the annular space defined between the walls. The coil spring may also be received within the annular slot defined between the inner wall 221 and outer wall 223 of the needle hub 220 to axially and torsionally bias the needle hub 220 and needle shield 240. It will, however, be appreciated that the spring may alternatively be positioned on the inside of the inner wall 221.

As in the previous embodiment, the needle hub 220 is provided with an internal thread 224 at its rearward end for attachment to an injection device in use. In this embodiment the cooperating features of the needle hub 220 comprise 3 circumferentially spaced apart bosses 225a, 225b and 225c. The bosses project inwardly from the inner surface of the outer wall 223. A cut-out 227 may be provided in the inner wall 221 adjacent to each boss 225 so as to provide a gap for the radially inward deflection of a latch member 251 on the needle shield 240 during assembly of the needle assembly 210.

The needle shield 240 includes a forward skin facing surface 260 (which may include a textured surface such as that shown in the first embodiment) and is provided with a central aperture 262 through which the needle connected to the needle hub 220 may project during use. The cooperating features 250a, 250b and 250c of the needle shied 240 comprise a track which includes a first slot 252, a second slot 254 and a latch area 255. At the rearward end of the track the first 252 and second 254 slots are separated by a rib 253. The rib 253 protrudes radially inwardly and extends axially along part of the track 250. A resiliently deformable tab 251 is provided at the rearward end of the first slot 252 and is arranged to deflect radially inward so as to pass over the boss 225 when the shield 240 and hub 220 are initially brought together (so that the boss 225 can be positioned within the track 250).

FIG. 8 shows the operational sequence of the needle assembly 210 according to a second embodiment. It may be noted that the coil spring has been omitted in these figures (purely for the purpose of clarity) and it will be appreciated that the spring would be provided between the needle hub 220 and needle shield 240 in a similar manner to the first embodiment so as to both rotationally and axially bias the components. In the initial position shown in FIG. 8(a), the boss 225 is positioned in the first slot 252 the coil spring biases the needle hub 220 and needle shield 240 to the extended position and the boss abuts the tab 251 to prevents over expansion or removal of the needle shield 240. As the needle shield 240 is pressed against the skin it moves towards the retracted position shown in FIG. 8(b) (compressing the coil spring). When moving towards this position the boss 225 passes beyond the axially extent of the rib 253 which separates the first slot 252 and second slot 254 of the track 250. As such, the needle shield 240 may rotate up to the needle hub 220 under the force of the torsional bias provided by the spring. This brings the needle shield 240 and needle hub 220 into the second rotational alignment when the boss 225 meets the side wall of the second slot 254. As the user removes the injection device from the skin the needle shield 240 moves back towards its extended position under the force of the axial bias of the coil spring as shown in FIG. 8(c). Axial movement brings the boss 225 into alignment with the latch portion 255 of the track 250. As the latch section 255 is positioned to the side of the second slot 254 the spring may further rotate the shield 240 in the biased direction relative to the hub 220 such that the boss moves into the latch section 255 (thus the hub 220 and shield 240 are in a third rotational alignment). In this position the needle shield 240 is locked against further movement towards the retracted position (with axial movement being blocked by the front and rear walls of the latch section of the track and the spring resisting rotation out of the latch).

Figure 9A:
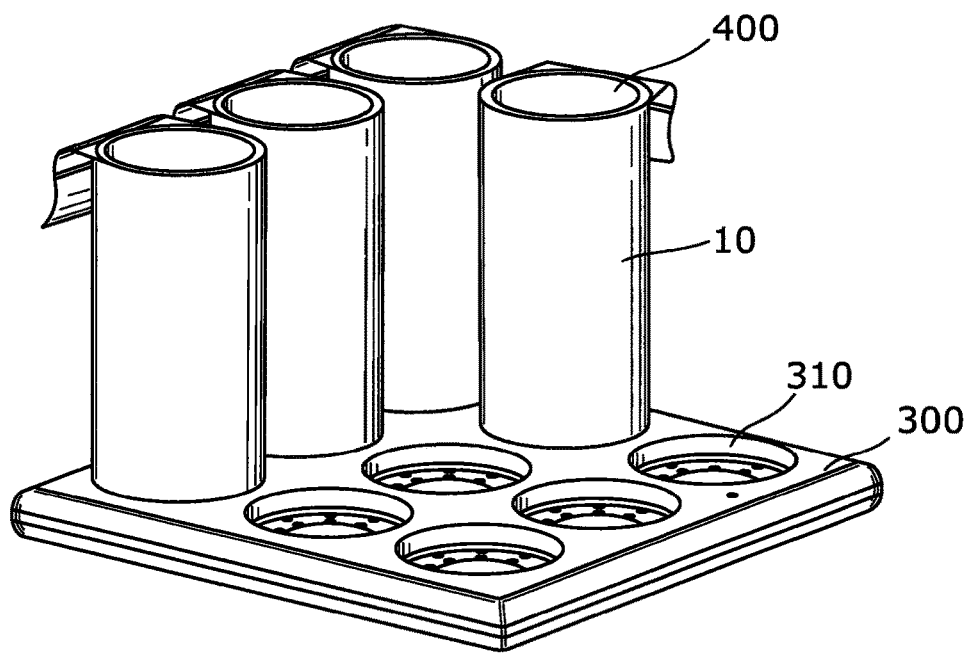
FIG. 9 shows an alternative packaging arrangement for a needle assembly in accordance with an embodiment.
Figure 9B:
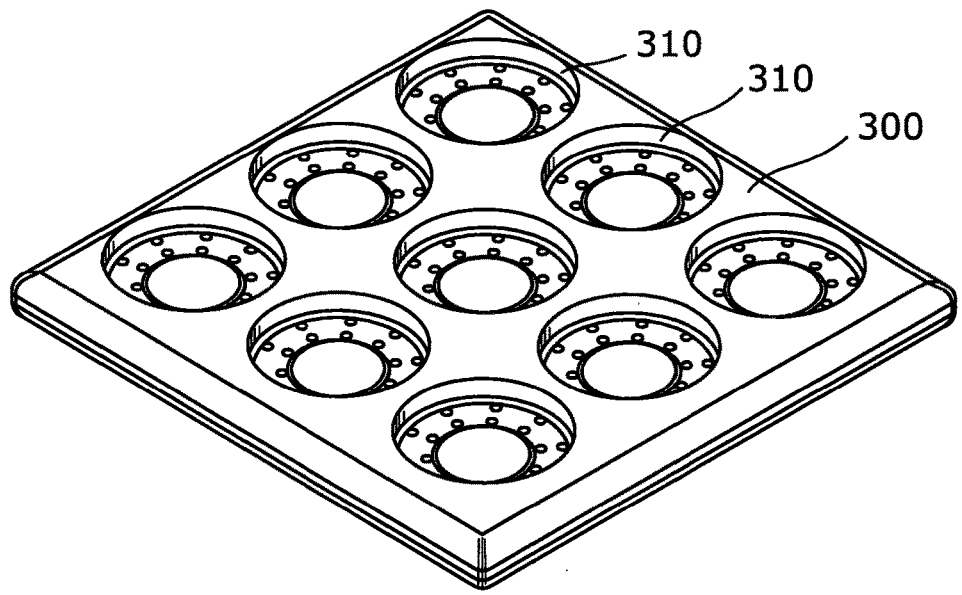

FIG. 9 illustrates a method of providing a plurality of needle assemblies (which may be needle assemblies in accordance with an embodiment of the invention). The needle assemblies are provided in a kit comprising a tray 300 formed with a plurality of recesses 310 each of which is configured to receive a single needle assembly 10. The recesses 310 are formed with a female profile corresponding to the forward end of the needle assembly 10. The recesses are intended to sealingly receive the needle assembly 10. Advantageously, in embodiments of the invention the needle assembly may be arranged such that all of the interconnecting features are formed on the inside of the shield means and the needle hub and needle are fully captive within the shield during storage. Thus, only the two end surfaces of the needle assembly 10 need to be sealed and the outer body of the needle shield may act as a sterile barrier. This may both simplify packaging and reduce the number of component parts. In particular, when provided in the tray arrangement of FIG. 9 the needle assembly 10 may seemingly engage with the tray 300 and a conventional "tear off" seal 400 may be provided on the other end of the needle assembly. The provision of needle assemblies in a tray may also help the user to track the usage of their needle assemblies.

Figure 10:
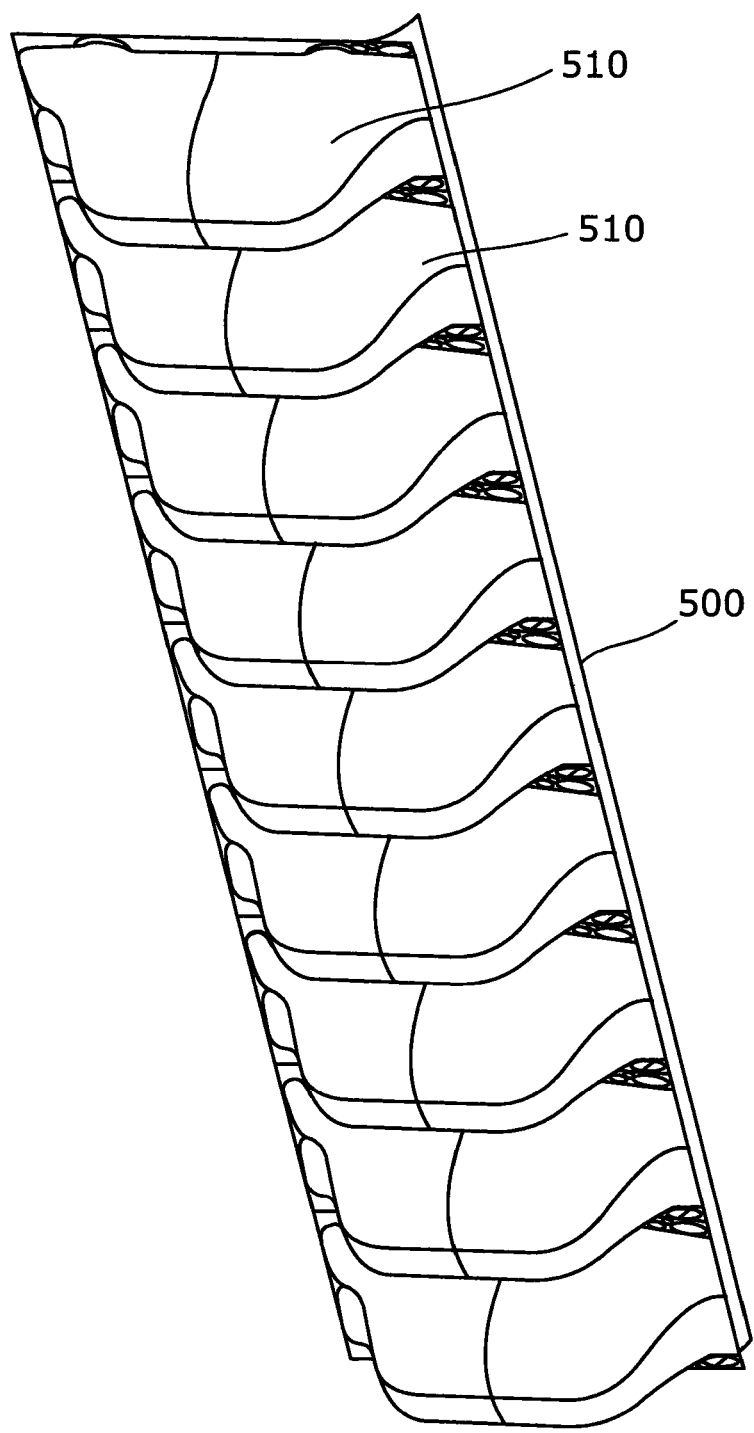
FIG. 10 shows a further packaging alternative for needle assemblies according to the embodiments of the invention.

Alternatively, the needle assemblies may be individually wrapped as shown in FIG. 10 and may be provided as a strip 500 comprising a plurality of packaged needle assemblies 510.

Figure 11A:
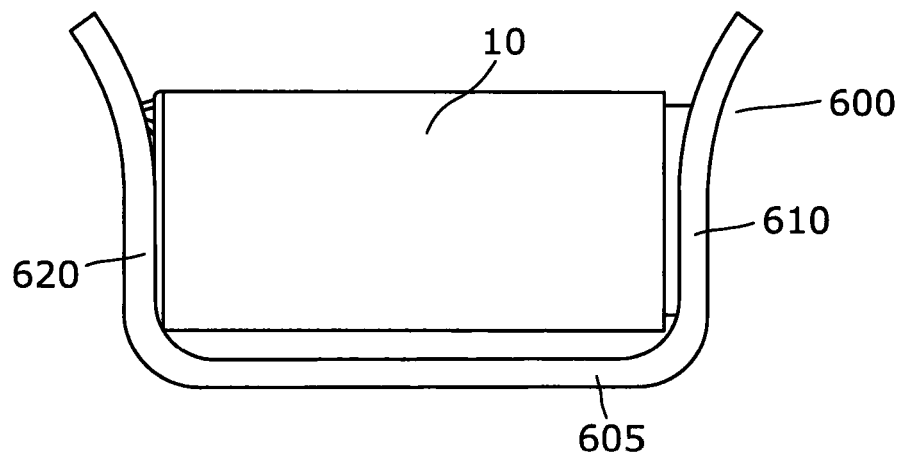
FIG. 11 shows a needle assembly and cap according to an embodiment of the invention.
Figure 11B:
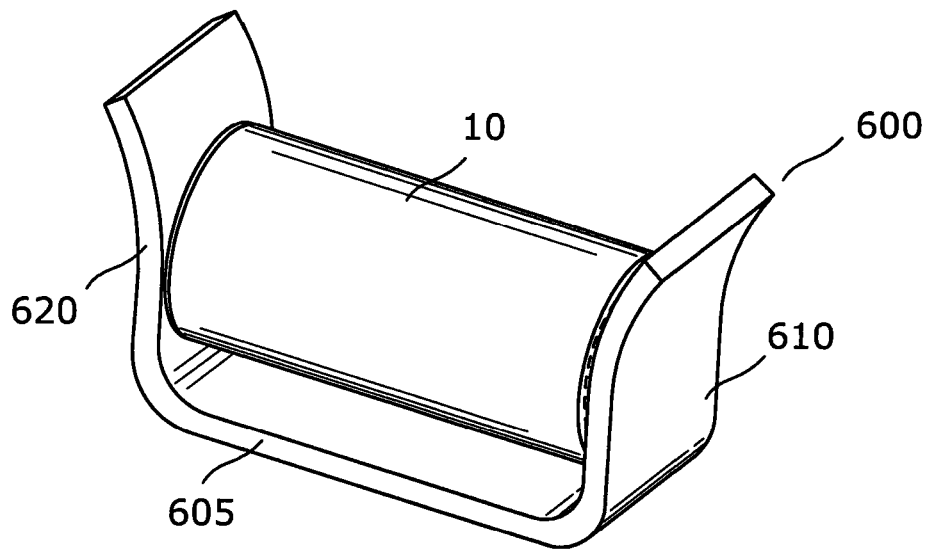

Alternatively or additionally, the needle assembly 10 may be provided with a cap 600 as shown in FIG. 11. The cap may be arranged to seal both ends of the device by having first 610 and second 620 spaced apart sealing members connected by an axial joining member 645. The sealing members 610 and 620 generally extend in a plane which is radial with respect to the needle assembly (when the cap is engaged with the assembly). The sealing members may be tapered or splay outwardly (to assist removal/engagement between the cap and the needle assembly). The inner surface of each of the end members 610 and 620 may be formed so as to resiliently engage the ends of the needle assembly 10. The needle assembly 10 may be easily removed from the cap by pulling the cap 600 and needle assembly 10 apart in a transverse (generally radial) direction. As the removal is in the radial direction it will not apply any force in the axial direction on the components of the needle assembly. The needle cap 600 can resiliently engage the needle assembly 10 such that it may be used both as a sealing member prior to use and a means for recovering the needle assembly 10 prior to disposal (i.e., to help further avoid any risk of needle stick injuries). Whilst the embodiment shown has only a single cap 600 it will also be appreciated that a plurality of cap members 600 could be joined together in order to supply a plurality of needle assemblies in a similar manner to the embodiment of FIG. 9.

Although the invention has been described above with reference to one or more preferred embodiments, it will be appreciated that various changes or modifications may be made without departing from the scope of the invention as defined in the appended claims.

For example, the needle assembly 210 of the second embodiment does not include an arrangement in which the needle hub 220 is fully contained within the needle shield 220. However, the skilled person will readily appreciate that the function of the cooperating features of the needle hub in that embodiment could be used in an arrangement such as that of the needle assembly 10 220

The invention claimed is:

1. A needle assembly, comprising:
a needle shield having a forward end and defining a slot including a radially ramped portion;
a needle hub disposed in the needle shield and having a resiliently deformable leg; and
a needle engaged with the needle hub and having a tip, wherein:
the needle hub is axially slidable in the needle shield from a retracted position to an extended position,
when the needle hub is in the retracted position,
the tip is disposed in the needle shield, and
the resiliently deformable leg is disposed in the radially ramped slot to rotationally fix the needle hub relative to the needle shield,
when the needle hub is in the extended position,
the tip extends beyond the forward end, and
the needle hub is rotatable in the needle shield between a first rotational position and a second rotational position,
the needle hub is axially biased toward the retracted position, and
the needle hub is torsionally biased toward the second rotational position.

2. The needle assembly of claim 1, further comprising a spring member to torsionally and axially bias the needle shield relative to the needle hub.

3. The needle assembly of claim 2, wherein the spring member is a coil spring.

4. The needle assembly of claim 3, wherein when the needle hub moves from the retracted position toward the extended position, the resiliently deformable leg flexes radially in the radially ramped portion of the slot.

5. The needle assembly of claim 4, wherein:
the slot of the needle shield further includes a flat portion, and
the radially ramped portion of the slot and the flat portion of the slot are connected and collinear.

6. The needle assembly of claim 3, wherein:
the resiliently deformable leg is one of a plurality of resiliently deformable legs spaced circumferentially about the needle hub, and
the slot is one of a plurality of slots spaced circumferentially within the needle shield,
wherein each of the plurality of slots includes a radially ramped portion.

7. The needle assembly of claim 1, wherein axial movement of the needle toward the extended position rotationally releases the needle hub from the radially ramped portion of the slot.

8. The needle assembly of claim 7, wherein:
the needle shield defines a second slot,
when the needle hub is rotationally biased in the second rotational position and slidably returns from the extended position to the retracted position, the resiliently deformable leg snaps into the second slot, and
the second slot provides an axial stop to the resiliently deformable leg to axially fix the needle hub relative to the needle shield.

9. The needle assembly of claim 1, wherein a forward facing surface of the needle shield comprises a textured surface.

10. The needle assembly of claim 9, wherein the textured surface comprises a plurality of forwardly projecting spikes.

11. The needle assembly of claim 1, wherein:
the needle shield has an inward projection opposite the forward end, and
the needle hub is captured in the needle shield between the forward end and the inward projection.

12. A needle assembly, comprising:
a needle shield defining a slot including a radially ramped portion; and
a needle hub disposed in the needle shield, having a resiliently deformable leg selectively slidably disposed in the radially ramped portion of the slot, and carrying a needle, the needle hub being
selectively slidable relative to the needle shield, and
selectively rotatable relative to the needle shield.

13. The needle assembly of claim 12, wherein the needle hub is rotationally fixed relative to the needle shield when the resiliently deformable leg is disposed in the radially ramped portion of the slot.

14. The needle assembly of claim 12, wherein the needle hub is rotatable relative to the needle shield when the resiliently deformable leg is released from the radially ramped portion of the slot.

15. The needle assembly of claim 12, wherein:
the needle shield defines a second slot,
the needle hub is axially and rotationally fixed relative to the needle shield when the resiliently deformable leg is disposed in the second slot.

16. The needle assembly of claim 12, wherein:
the needle has a tip,
the needle shield has a forward end,
the needle hub is selectively slidable relative to the needle shield between
a retracted position and
an extended position,
the tip is disposed in the needle shield when the needle hub is in the retracted position, and
the needle extends through the forward end when the needle hub is in the extended position.

17. The needle assembly of claim 12, further comprising a spring torsionally and axially biasing the needle hub relative to the needle shield.

18. A needle assembly comprising:
a needle shield having a resiliently deformable leg; and
a needle hub disposed in the needle shield, carrying a needle, and defining a slot including a radially ramped portion to selectively slidably receive the resiliently deformable leg, the needle hub being
selectively slidable relative to the needle shield, and
selectively rotatable relative to the needle shield.

19. The needle assembly of claim 18, wherein the needle hub is rotationally fixed relative to the needle shield when the resiliently deformable leg is disposed in the radially ramped portion of the slot.

20. The needle assembly of claim 18, wherein the needle hub is rotatable relative to the needle shield when the resiliently deformable leg is released from the radially ramped portion of the slot.

* * * * *